United States Patent [19]

Jolles et al.

[11] Patent Number: 4,943,562
[45] Date of Patent: Jul. 24, 1990

[54] TETRA- AND PENTAPEPTIDES CONTAINING THE LYSYL-ARGINYL-ASPARTYL SEQUENCE AND THEIR APPLICATIONS AS MEDICINES, PARTICULARLY ANTI-THROMBOTIC MEDICINES

[75] Inventors: Pierre Jolles, Paris; Anne-Marie Fiat, Le Vesinet; Claudine Soria, Taverny; Levy-Toledano Sylviane, Paris, all of France; Sanghamitra Raha, Calcutta, India; Elisabeth Mazoyer, Paris; Ludovic Drouet, Bourg-la-Reine, both of France

[73] Assignees: Institut des Vaisseaux et du Sang; Centre National de la Recherche Scientifique, both of Paris, France

[21] Appl. No.: 263,859

[22] Filed: Oct. 28, 1988

[30] Foreign Application Priority Data

Oct. 30, 1987 [FR] France .................. 87 15061

[51] Int. Cl.$^5$ .................. A61K 37/02; C07K 7/06
[52] U.S. Cl. .................. 514/18; 514/17; 514/18; 530/329; 530/330
[58] Field of Search .................. 530/330, 329; 514/17, 514/18

[56] References Cited

U.S. PATENT DOCUMENTS

| | | | |
|---|---|---|---|
| 4,190,646 | 2/1980 | Goldstein et al. | 530/330 |
| 4,190,647 | 2/1980 | Goldstein et al. | 530/330 |
| 4,298,523 | 11/1981 | Heavner | 530/330 |
| 4,305,852 | 12/1981 | Garsky | 530/330 |
| 4,428,938 | 1/1984 | Kisfaludy et al. | 514/18 |
| 4,683,291 | 7/1987 | Zimmerman et al. | 530/330 |
| 4,792,525 | 12/1988 | Ruoslahti et al. | 530/330 |

OTHER PUBLICATIONS

Sanghamitra Raha et al., "KRDS-A Tetrapeptide Derived From Lactotransferrin-Inhibits Binding of Monoclonal Antibody Against Glycoprotein IIb-IIIa on ADP-Stimulated Platelets and Megakaryocytes", Blood, vol. 72, No. 1, Jul. 1988, pp. 172-178.
Blood, Nov. 1986, No. 1150, Eur. J. Biochem. 158, 379-382 (1986).
Eur. J. Biochem. 145, 659-676 (1984) Blood, 67, 285-293 (1986).
J. Biol. Chem. 258, 12582-12586 (1983) Blood, 69, 570-577 (1987); and Thromb. Haemost. 58, 243A (1987).
Chemical Abstracts, vol. 109, 1988 No. 12647w.

*Primary Examiner*—Lester L. Lee
*Attorney, Agent, or Firm*—Fleit, Jacobson, Cohn, Price, Holman & Stern

[57] ABSTRACT

The peptides according to the invention are of the following general formula I:

Z-Lys-Arg-Asp-X-Y  (I)

wherein:
X is the residue of one of the 20 common aminoacids in the L-configuration,
Y is hydroxyl or the C-terminal residue of one of the 20 common aminoacids in the L-configuration,
Z is acetyl, hydrogen or the N-terminal residue of one of the 20 common aminoacids in the L-configuration, as the case may be N-acetylated, whereby it is understood that:
when Y is the C-terminal residue of one of the 20 common aminoacids in the L-configuration, Z is acetyl or hydrogen and
X can in all cases be different from Y and from Z.

Application to the preparation of anti-thrombotic medicines.

14 Claims, No Drawings

TETRA- AND PENTAPEPTIDES CONTAINING THE LYSYL-ARGINYL-ASPARTYL SEQUENCE AND THEIR APPLICATIONS AS MEDICINES, PARTICULARLY ANTI-THROMBOTIC MEDICINES

The object of the present invention is to provide new tetra- and pentapeptides with anti-thrombotic activity.

More precisely, the invention relates to tetra- and pentapeptides containing the Lys-Arg-Asp sequence and their therapeutic applications, particularly as anti-thrombotic agents.

It should be understood that in the aforesaid statement as well as in the following description and claims, all peptides are represented with the amino-terminal residue on the left and all of them are in the L-configuration.

A large amount of facts, gathered in the course of the latest years tend to indicate that the fibrinogen receptor is situated on a complex of two platelet glycoproteins GP IIb and GP IIIa, on the plasma membrane of the platelets. The fibrinogen binding onto the platelet receptor requires the activating of the platelets by agonists such as ADP, thrombin, etc., which seems to result in exposing the fibrinogen binding sites (see for example W. M. Isenberg et al in Blood, Nov. 1986, n. 1150).

A synthetic tetrapeptide Arg-Gly-Asp-Ser containing the Arg-Gly-Asp sequence common to sequences of the fibrinogen α-chain, of the von Willebrand factor (vWF) and of the fibronectin and a sequence (400–411) of the fibrinogen γ chain are known as fibrinogen binding inhibitors. Pierre JOLLES et al (Eur. J. Biochem. 158, 379–382 (1986)) have noted similarities between peptidic sequences fo the fibrinogen γ-chain (400–411) and of casein K (106–116) obtained from cow milk casein in their ability to inhibit platelet aggregation and fibrinogen binding. However, the effects of these inhibitory peptidic sequences on the binding of monoclonal antibodies directed against the glycoproteic complex GP IIb-IIIa have not been studied.

In view of this fact, the Applicants while pursuing investigations made in this field, conceived the idea of synthesizing and studying the pharmacological activity of a family of tetra- and pentapeptides containing the Lys-Arg-Asp sequence, and particularly the Lys-Arg-Asp-Ser tetrapeptide which corresponds to the 39→42 sequence of human lactotransferrin whose complete aminoacid sequence established in the "Laboratoire des Proteines" (Protein Laboratory), directed by Professor Pierre JOLLES, at the University of Paris V, is described by Marie-Héléne METZ-BOUTIGUE et al. in Eur. J. Biochem., 145, 659–676 (1984).

According to one of its aspects, the object of this invention relates to a peptide of the following general formula:

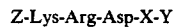  (I)

wherein:
- X is the residue of one of the 20 common aminoacids in the L-configuration,
- Y is hydroxyl or the C-terminal residue of one of the 20 common aminoacids in the L-configuration,
- Z is acetyl, hydrogen or the N-terminal residue of one of the 20 common aminoacids in the L-configuration, as the case may be N-acetylated, whereby it is understood that:

when Y is the C-terminal residue of one of the 20 common aminoacids in the L-configuration, Z is acetyl or hydrogen and X can in all cases be different from Y and from Z.

It is reminded that the "20 common aminoacids" are: alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophane (Trp); tyrosine (Tyr); and valine (Val).

The peptides of general formula I can be obtained by conventional peptidic synthesis or, more simply, by employing a peptide synthesizer.

As can be seen from the statement incorporated in the experimental part of the description hereinafter, the peptides according to the invention are not only capable of inhibiting platelet aggregation and fibrinogen binding onto stimulated platelets, but are also capable of inhibiting the binding of monoclonal antibodies directed against the GP IIb-GP IIIa complex onto stimulated platelets.

Besides, the peptides according to the invention, and particularly those of the general formula:

  (II), act synergetically with other known peptides having an anti-thrombotic activity, in particular with the Arg-Gly-Asp-Ser peptide.

Furthermore, megacaryocytes (MK), in the same manner as platelets, can be stimulated by ADP in order to expose the binding sites to these peptides and this ability is restricted to a group of megacaryocytes which are predominantly mature, judging from morphological criteria.

In view of these properties, the peptides of general formula I according to the invention can be used for therapeutical purposes, particularly in the prevention and treatment of thromboses, alone or in admixture together and/or with other known peptides having an anti-thrombotic activity.

They can then be administered, together with at least one substance selected from among the usual inert diluents, adjuvants and excipients, by intravenous, intramuscular, hypodermic, sub-cutaneous, intranasal, and as the case may be, oral or rectal ways, or also under the form of liposomes.

The doses administered will generally range from 0.05 to 5 mg/kg of body weight, 3 to 5 times a day.

The following statement is intended to better explain the invention.

I. Examples of synthesis and purification:

A. Synthesis, purification and analysis of Lys-Arg-Asp-Ser peptide (peptide 1)

This peptide was synthesized by means of the peptide synthesizer manufactured by "Applied Biosystems" and sold under the reference 430A.

It was then purified by high performance liquid chromatography (HPLC) under the following conditions:
- Column: 4.5×300 mm, grafted silica, reverse phase, porosity 100 Å, diameter of particles 5 μm, sold under the trade name Nucleosil ® C 18 by MACHEREY NAGEL.
- Eluent: water/acetonitril/trifluoroacetic acid in the proportions by volume of 970:30:1.

Flowrate: 1 ml/min.
Reading at 215 nm.

The peptide was eluted after 4.76 minutes. It was then subjected to freeze-drying.

Analysis

After a thorough hydrolysis by 6N HCl+2-mercapto ethanol concentrated at 1/2,000, for 18 hours at 110° C. under vacuum, it was found that the aminoacid composition (residues/mole) was as follows:

Asp: 1.04
Ser: 0.91
Lys: 1.02
Arg: 0.92 using a Biotronik ® apparatus, model LC 6000 sold by SEMSA BIOTRONIK.

The peptide sequence was established by means of the sequencer manufactured by "Applied Biosystems", reference 470A.

The phenylthiohydantoins (PTH) of the aminoacids were identified by HPLC with the chromatograph manufactured by "Applied Biosystems", reference 120A.

The sequence found is as follows:

Lys — Arg — Asp — Ser *

\* ___ : aminoacid determined by the automated Edman degradation.

No traces of impurity could be detected. This peptide is therefore at least 99% pure.

Physical characteristics:

This peptide is hydrophilic and its water-solubility is very good.

B. Synthesis, purification and analysis of other peptides of general formula I

The other peptides of general formula I can be synthesized, purified and analyzed in a similar way as already described as regards the Lys-Arg-Asp-Ser peptide.

Hereunder are given, by way of examples, the analysis results obtained for the peptides:

Lys-Arg-Asp-Tyr (X=Tyr, Y=OH and Z=H) (peptide 2), Tyr-Lys-Arg-Asp-Ser (X=Ser, Y=OH and Z=Tyr) (peptide 3), Ac-Lys-Arg-Asp-Ser-Lys (X=Ser, Y=Lys and Z=Ac) (peptide 4), Lys-Arg-Asp-Ser-Tyr (X=Ser, Y=Tyr and Z=H) (peptide 5) and Lys-Arg-Asp-Arg (X=Arg, Y=OH and Z=H) (peptide 6).

The aminoacid compositions found are gathered in the following Table:

| No of the peptide | Aminoacid residue | | | | |
|---|---|---|---|---|---|
| | Asp | Ser | Tyr | Lys | Arg |
| 2 | 0.99 | — | 0.99 | 0.99 | 1.02 |
| 3 | 1.00 | 1.00 | 0.99 | 1.00 | 1.05 |
| 4 | 0.89 | 0.86 | — | 2.09 | 1.02 |
| 5 | 0.96 | 0.81 | 1.02 | 1.09 | 1.12 |
| 6 | 1.00 | — | — | 1.05 | 1.99 |

The sequences found by the automated Edman degradation are as follows:

Peptide 2    Lys — Arg — Asp — Tyr

Peptide 3    Tyr — Lys — Arg — Asp — Ser

Peptide 4    nothing found "directly"

Peptide 5    Lys — Arg — Asp — Ser — Tyr

Peptide 6    Lys 138 — Arg — Asp — Arg

After a trypsic hydrolysis, the sequence found for peptide 4 is:

Arg — Asp — Ser — Lys

II. Pharmacological study:

A. "In vitro" studies

1. Comparative study with known peptides

A comparative study as performed involving tetrapeptide 1, Lys-Arg-Asp-Ser, on the one hand, and two peptides known as having an inhibitory acitivity versus the fibrinogen binding, namely the aforesaid Arg-Gly-Asp-Ser peptide and the VL 10 peptide which represents the ten terminal aminoacids of the C-terminal portion of the fibrinogen γ-chain, on the other hand, concerning certain pharmacological activities.

More precisely, the study covered platelet aggregation, ADP induced fibrinogen binding and the binding of monoclonal antibodies directed against the glycoproteins GP IIb-IIIa onto human platelets. The binding of a monoclonal antibody against the glycoproteinic complex GP IIb-IIIa onto the human megacaryocytes (MK) was also studied following a treatment by means of the platelet-inhibitory peptides. The binding of the monoclonal antibodies onto the platelets and megacaryocytes was visualized and qualitatively evaluated by an indirect method with immunoperoxidase [Beckstead et al., Blood, 67, 285 (1986)].

A 1 mM concentration of peptide 1, well-nigh completely inhibits both platelet aggregation and ADP induced fibrinogen binding. Among the three peptides under study, only peptide 1 according to the invention (at a concentration of 450 or preferably 900 μM) inhibits the binding of monoclonal antibodies directed against the GP IIb-IIIa complex, viz. in connection with the present study, the monoclonal antibodies AP2 and P2 which are both of them directed against an epitope of the platelet membrane and is constituted by the complex of glycoproteins IIb and IIIa.

In this respect, it should be pointed out that antibody AP2 is a mouse monoclonal antibody against the human IIb-IIIa platelet glycoproteinic complex [Pidard et al., J. Biol. Chem., 258, 12582 (1983)] and antibody P2 is a mouse monoclonal antibody against the human IIb-IIIa glycoproteinic complex, prepared and sold by IMMUNOTECH of Marseille (France).

This property of peptide 1 according to the invention was only evidenced on the platelets stimulated by ADP and not on the non-stimulated platelets. Although the binding both of AP2 and P2 is inhibited by peptide 1, the binding of P2 is considerably more affected than the one of AP2.

The binding of monoclonal antibodies produced in SüCHOW in the Popular Republic of China, namely the monoclonal antibody of a mouse SZ2 directed against the human Ib platelet glycoprotein [Ruan et al., Blood, 69, 570, (1987)], the monoclonal antibody SZ21 directed against the human IIIa platelet glycoprotein and the monoclonal antibody of a mouse SZ22 directed against the human IIb platelet glycoprotein [Ruan et al., Thromb. Haemost. 58, 243A, (1987)] is not inhibited by peptide 1.

The binding of radio-iodinated AP2 onto platelets stimulated by ADP is reduced by 30% through a pre-treatment with peptide 1, as compared with the platelets which are incubated with peptide 1 in which absence of stimulation by ADP.

Peptide 1 also inhibits the binding of P2 onto part of the megacaryocytes, after a stimulation by ADP. The inhibition of the binding of P2 onto the MK's requires a higher concentration of ADP (15 or 20 $\mu$M) than in the case of platelets (5 $\mu$M), which relfects a lower response of the MK's to ADP. Only a small percentage of the total population of MK's (21%) exhibits an inhibition of the binding of P2. The percentage of MK's exhibiting an inhibition, also among the mature MK's is significantly higher ($P<0.001$) than the one observed among the MK's in the course of maturation.

These data demonstrate that peptide 1 according to the invention is capable of inhibiting not only platelet aggregation and fibrinogen binding onto stimulated platelets, but also the binding of a monoclonal antibody directed against the GP IIb-IIIa complex onto stimulated megacaryocytes.

In addition, the MK's just like the platelets, can be stimulated by ADP to expose the binding sites to peptide 1 and this ability is restricted to a portion of the MK's which are predominantly mature, judging from the morphological criteria.

2. Specific "in vitro" action on platelet activation and independent phosphorylation This study was also carried out on Lys-Arg-Asp-Ser peptide (peptide 1).

With a view to understanding its mechanism of action, investigations were made in order to find out whether it interfered with the mechanism of transduction of the membrane signal. Actually, it was established that whenever an agonist such as thrombin binds to the platelet membrane, it activates a phospholipase, viz. phospholipase C (PLC) which hydrolyzes phosphatidylinositol 4,5 bis-phosphate (PIP$_2$) which is a constituent of the membrane. This gives rise to two very important messengers: diacylglycerol (DAG) and inositol trisphosphate (IP$_3$).

Besides, DAG generates phosphatidic acid (PA), but primarily activates protein kinase C that phosphorylates a protein with a molecular weight of 43,000 (P43).

The phosphorylated protein P43 plays a role in the releasing reaction.

Peptide 1 inhibits aggregation to thrombin. The inhibition of aggregation to thrombin is accompanied with an inhibition of the serotonine release in the same order to magnitude: 50 to 60%, with a 1000 $\mu$M concentration of peptide 1.

However, peptide 1 on the one hand, does not affect the activity of PLC since PIP$_2$ is hydrolyzed and PA synthesized and, on the other hand, it does not modify the phosphorylation of P43 which takes place in the presence of thrombin.

The uniqueness of this peptide, and of the peptides according to the invention in general, is therefore to inhibit the platelet releasing reaction while maintaining an activity of PLC as well as a phosphorylation of P43.

3. Compared inhibitory activity of different peptides according to the invention on ADP induced platelet aggregation This activity was measured "in vitro" with 1000 $\mu$M concentrations of each of the peptides involved.

The results obtained are gathered in the following Table:

| Peptide (n°) | Platelet aggregation inhibition in % |
| --- | --- |
| Lys-Arg-Asp-Ser (1) | 90 |
| Lys-Arg-Asp-Tyr (2) | 30 |
| Tyr-Lys-Arg-Asp-Ser (3) | 55 |
| Ac-Lys-Arg-Asp-Ser-Lys (4) | 67 |
| Lys-Arg-Asp-Ser-Tyr (5) | 60 |

B. "In vivo" studies

1. Anti-thrombotic activity

Experimental work on thrombosis carried out on two different animal species (rat and guineapig) have shown that the peptides according to the invention, in particular the peptides of the general formula Lys-Arg-Asp-X (II), viz. particularly peptide Lys-Arg-Asp-Ser (peptide 1) and peptide Lys-Arg-Asp-Arg (peptide 6), exert an anti-thrombotic activity on an intravascular thrombus induced by a specific lesion of the arterial wall. The type of thrombus which is thus induced takes into account the participation of the blood platelets against which the peptide exerts its activity but also the reactivity of the injured vascular wall.

This anti-thrombotic activity "in vivo" was demonstrated as follows:

following an injection of the peptide involved by direct intravenous way;

with concentrations as low as 0.5 mg/kg of weight of the animal under experiment.

This anti-thrombotic effect lasts more than 80 minutes following the injection. It fades away with excessively high concentrations (superior to 5 mg/kg of animal weight).

2. Synergetic activity along with other antithrombotic peptides

In the same experimental thrombosis system, when a peptide according to the invention is used, particularly a peptide of the formula Lys-Arg-Asp-X (II) and a known peptide having an anti-thrombotic activity such as in particular peptide Arg-Gly-Asp-Ser, with very low concentrations, a very strong and lasting inhibition versus the formation of thrombi can be observed, whereas double doses of each of the peptides involved, used separately, do not yield any effect or if so, only a nominal effect of a very short duration time.

Consequently, the fast simultaneous injection of 250 $\mu$g/kg of peptide Arg-Gly-Asp-Ser and 125 $\mu$g/kg of peptide Lys-Arg-Asp-Ser in the rat inhibits the formation of thrombi on a 70% basis for a period of up to 70 minutes.

In return, the injection in the same animal of 250 $\mu$g/kg of a peptide according to the invention (Lys-Arg-Asp-Ser) does not generate any inhibition, whereas the injection of 500 $\mu$g/kg of peptide Arg-Gly-Asp-Ser generates a very nominal inhibition only, which lasts a few minutes only.

To conclude with, the results obtained both "in vitro" and "in vivo" show that the peptides according to the invention, and in particular the peptides of general formula Lys-Arg-Asp-X (II), while probably acting on the blood platelets, inhibit the capability of these cells to interact in a normal way and thereby constitute anti-thrombotic molecules.

We claim:

1. A peptide of the formula I:

Z-Lys-Arg-Asp-X-Y    (I)

wherein:
    X is the residue of an amino acid in the L-configuration selected from the group consisting of Ala, Arg, Asn, Asp, Cys, Gln, Glu, Gly, His, Ile, Leu, Lys, Met, Phe, Pro, Ser, Thr, Trp and Tyr,
    Y is hydroxyl or the C-terminal residue of an amino acid in the L-configuration selected from the group consisting of Ala, Arg, Asn, Asp, Cys, Gln, Glu, His, Ile, Leu, Lys, Met, Phe, Pro, Ser, Thr, Trp, Tyr and Val,
    Z is acetyl, hydrogen or the N-terminal residue of an amino acid in the L-configuration selected from the group consisting of Ala, Arg, Asn, Asp, Cys, Gln, Glu, Gly, His, Ile, Leu, Lys, Met, Phe, Pro, Ser, Thr, Trp, Tyr and Val, N-acetylated or not N-acetylated;
    with the provisos that:
    when Y is the C-terminal residue of an amino acid in the L-configuration, Z is acetyl or hydrogen, and
    X can in all cases be different from Y and from Z.

2. A peptide according to claim 1 of the formula II:

Lys-Arg-Asp-X    (II)

wherein X is the residue of an amino acid selected from the group consisting of Ala, Arg, Asn, Asp, Cys, Gln, Glu, Gly, His, Ile, Leu, Lys, Met, Phe, Pro, Ser, Thr, Trp, and Tyr.

3. The peptide Lys-Arg-Asp-Ser.

4. A peptide from the group consisting of:
    Lys-Arg-Asp-Tyr;
    Tyr-Lys-Arg-Asp-Ser;
    Ac-Lys-Arg-Asp-Ser-Lys;
    Lys-Arg-Asp-Ser-Tyr; and
    Lys-Arg-Asp-Arg.

5. A therapeutic composition comprising, as active substance, an effective amount of at least one peptide according to claim 1 and a pharmaceutically acceptable carrier.

6. A therapeutic composition according to claim 5, further comprising, as a second active substance, a second compound having anti-thrombotic activity.

7. A therapeutic composition according to claim 6, wherein the second compound having anti-thrombotic activity is the peptide Arg-Gly-Asp-Ser.

8. A therapeutic composition according to claim 5, wherein the pharmaceutically acceptable carrier is at least one member selected from the group consisting of pharmaceutically acceptable inert diluents, adjuvants and excipients.

9. A therapeutic composition with anti-thrombotic activity, comprising an effective anti-thrombotic amount of at least one compound of the formula II:

Lys-Arg-Asp-X    (II), wherein X is an amino acid selected from the group consisting of Ala, Arg, Asn, Asp, Cys, Gln, Glu, Gly, His, Ile, Leu, Lys, Met, Phe, Pro, Ser, Thr, Trp and Tyr, and a pharmaceutically acceptable carrier.

10. A method of preventing or treating thrombosis, comprising the step of administering an effective anti-thrombotic amount of a peptide of the formula I:

Z-Lys-Arg-Asp-X-Y    (I)

wherein:
    X is the residue of an amino acid in the L-configuration selected from the group consisting of Ala, Arg, Asn, Asp, Cys, Gln, Glu, Gly, His, Ile, Leu, Lys, Met, Phe, Pro, Ser, Thr, Trp, Tyr and Val,
    Y is hydroxyl or the C-terminal residue of an amino acid in the L-configuration selected from the group consisting of Ala, Arg, Asn, Asp, Cys, Gln, Glu, Gly, His, Ile, Leu, Lys, Met, Phe, Pro, Ser, Thr, Trp, Tyr and Val,
    Z is acetyl, hydrogen or the N-terminal residue of amino acid in L-configuration selected from the group consisting of Ala, Arg, Asn, Asp, Cys, Gln, Glu, Gly, His, Ile, Leu, Lys, Met, Phe, Pro, Ser, Thr, Trp and Tyr and Val, N- acetylated or not N-acetylated;
    with the provisos that:
    when Y is the C-terminal residue of an amino acid in the L-configuration, Z is acetyl or hydrogen, and
    X can in all cases be different from and from Z.

11. A therapeutic composition comprising, as active substance, an effective anti-thrombotic amount of at least one peptide according to claim 1 and a pharmaceutically acceptable carrier.

12. A therapeutic composition according to claim 11, further comprising, as a second active substance, a second compound having anti-thrombotic activity.

13. A therapeutic composition according to claim 12, wherein the second compound having anti-thrombotic activity is the peptide Arg-Gly-Asp-Ser.

14. A therapeutic composition according to claim 11, wherein the pharmaceutically acceptable carrier is at least one member selected from the group consisting of pharmaceutically acceptable inert diluents, adjuvants and excipients.

* * * * *